United States Patent [19]

Protiva et al.

[11] 3,985,750

[45] Oct. 12, 1976

[54] FATTY ACID ESTERS OF 8-SUBSTITUTED 10-[4-(HYDROXYALKYL)PIPERAZINO]-10,11-DIHYDRODIBENZO[b,f]THIEPINS

[75] Inventors: Miroslav Protiva; Jiri Jilek; Karel Sindelar; Jirina Metysova, all of Praha, Czechoslovakia

[73] Assignee: SPOFA, Sdruzeni podniku pro zdravotnickou vyrobu, Prague, Czechoslovakia

[22] Filed: July 19, 1974

[21] Appl. No.: 490,218

Related U.S. Application Data

[63] Continuation-in-part of Ser. No. 166,644, July 27, 1971, abandoned.

[30] Foreign Application Priority Data

July 30, 1970    Czechoslovakia .................. 5300-70
Apr. 30, 1971    Czechoslovakia .................. 3162-71
May 10, 1971    Czechoslovakia .................. 3371-71

[52] U.S. Cl. ........................... 260/268 TR; 424/250
[51] Int. Cl.² ..................................... C07D 409/04
[58] Field of Search .......................... 260/268 TR

[56] References Cited
UNITED STATES PATENTS

| | | | |
|---|---|---|---|
| 3,600,391 | 8/1971 | Mastursi et al. | 260/268 TR |
| 3,600,392 | 8/1971 | Zust et al. | 260/268 TR |
| 3,681,354 | 8/1972 | Mastursi et al. | 260/268 TR |
| 3,830,814 | 8/1974 | Jilek et al. | 260/268 TR |
| 3,875,156 | 4/1975 | Blondel et al. | 260/243 |
| 3,875,158 | 4/1975 | Blondel et al. | 260/243 A |

FOREIGN PATENTS OR APPLICATIONS

| | | | |
|---|---|---|---|
| 1,123,400 | 8/1968 | United Kingdom | 260/268 TR |
| 1,136,527 | 12/1968 | United Kingdom | 260/268 TR |

*Primary Examiner*—Nicholas S. Rizzo
*Assistant Examiner*—Jose Tovar
*Attorney, Agent, or Firm*—Michael J. Striker

[57] ABSTRACT

Fatty acid esters of 8-substituted 10-[4-(hydroxyalkyl)piperazino]-10,11-dihydrodibenzo[b,f]-thiepins and oxepins having the formula

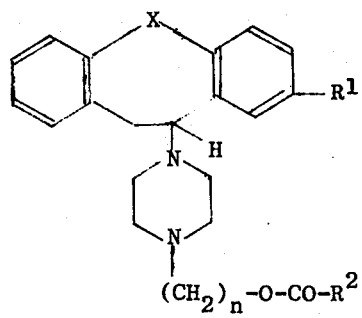

in which X is a sulfur or oxygen atom, $R^1$ is a hydrogen, chloro, or trifluoromethyl radical, a lower alkyl radical having at most 5 carbon atoms, or a cycloalkyl radical having at least 3 and at most 8 carbon atoms, or an alkoxy or alkylthio radical the alkyl moiety of which has at most 4 carbon atoms, $R^2$ is an alkyl radical having at least 5 and at most 17 carbon atoms, and n is 2, 3, or 4, and their salts with pharmaceutically acceptable inorganic and organic acids. The compounds have a high degree of neuroleptic activity and retain this activity for long periods after administration.

Related fatty acid esters of 8-substituted 10-[4-(hydroxyalkyl)-piperazino]dibenzo[b,f]thiepins and oxepins having the formula

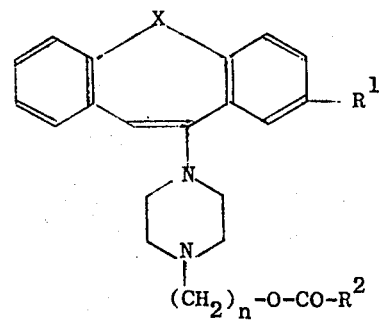

and fatty acid esters of 8-substituted 4-[4-(hydroxyalkyl)piperazino]thieno[2,3-b]-1-benzothiepins and oxepins having the formula

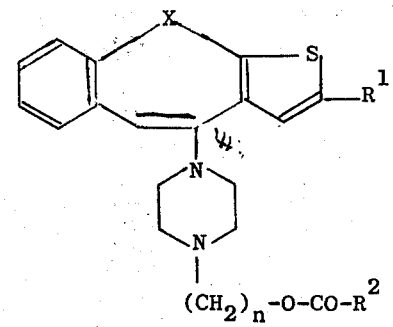

in which formulae X, $R^1$, $R^2$ and n each have the foregoing significance, are also included herein.

2 Claims, No Drawings

FATTY ACID ESTERS OF 8-SUBSTITUTED 10-[4-(HYDROXYALKYL)PIPERAZINO]-10,11-DIHYDRODIBENZO[B,F]THIEPINS

REFERENCE TO RELATED APPLICATION

This application is a continuation in part of our application Ser. No. 166,644, filed July 27, 1971 now abandoned.

SUMMARY OF THE INVENTION

The present invention pertains to a series of compounds which have been found to have neuroleptic activity of long duration after administration and to process for producing and using the same.

The compounds are esters of fatty or alkanoic acids and 8-substituted 10-[4-(hydroxyalkyl)piperazino]-10,11-dihydrodibenzo[b,f]thiepins and oxepins, esters of fatty acids and 8-substituted 10-[4-(hydroxyalkyl)-piperazino]dibenzo[b,f]thiepins and oxepins, and esters of fatty acids and 8-substituted [4-(4-hydroxyalkyl)piperazino]thieno[2,3-b]-1-benzothiepins and oxepins having the formulae:

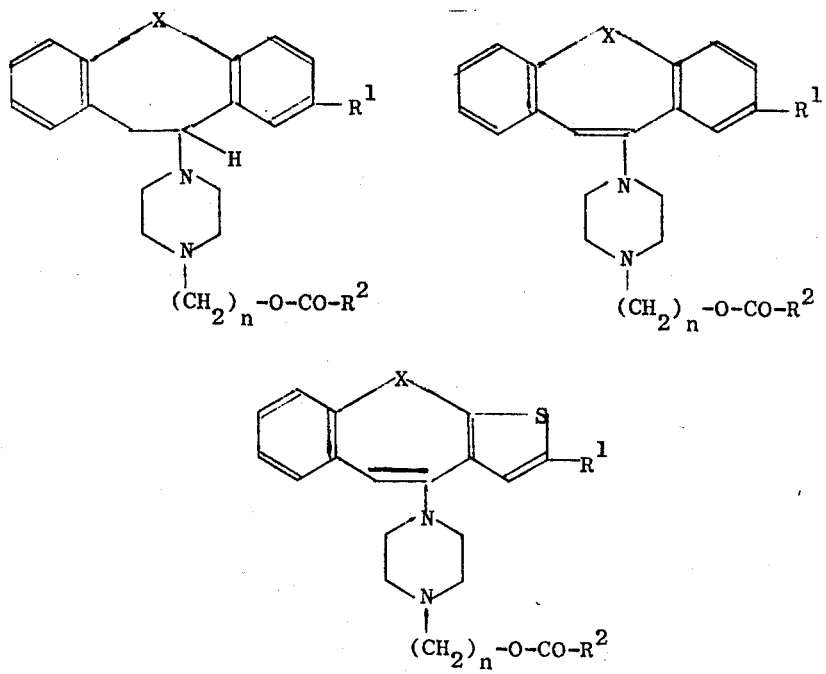

in each of which formulae X is a sulfur or oxygen atom, $R^1$ is a hydrogen, chloro, or trifluoromethyl radical, or a lower alkyl radical having at most 5 carbon atoms, or a cycloalkyl radical having at least 3 and at most 8 carbon atoms, or an alkoxy or alkylthio radical the alkyl moiety of which has at most 4 carbon atoms, $R^2$ is an alkyl radical having at least 5 and at most 17 carbon atoms, and n is 2, 3 or 4, and their salts with pharmaceutically acceptable inorganic and organic acids.

The compounds of the present invention are characterized by their high degree of neuroleptic activity and by the long duration of such activity when administered in the form of a suitable pharmaceutical composition. Suitable pharmaceutical compositions for intramuscular injection are solutions of the compounds in neutral vegetable oils. Pharmaceutical compositions containing these compounds are potentially useful for neuroleptic maintenance or supporting therapy in the treatment of chronic schizophrenia in humans. A single dose of such pharmaceutical compositions produces a high degree of activity which persists for several days.

This prolonged neuroleptic activity of the compounds of the present invention has been established in animal experiments. For example, 8-methylthio-10-[4-(3-octanoyloxypropyl)piperazino]-10,11-dihydrodibenzo[b,f]thiepin and 8-methylthio-10-[4-(3-decanoyloxypropyl)piperazino]-10,11-dihydrodibenzo[b,f]thiepin, whose preparations are described in Examples 5 and 13 hereinafter, when administered in a dose of 5 milligrams per kilogram of body weight intramuscularly as solutions in sunflower oil, produced in dogs an antiapomorphine emesis effect which persisted for a period of 14 and 19 days, respectively, that is during this period apomorphine enesis was blocked or inhibited. This test, which was described by P. A. J. Janssen and C. J. E. Niemegeers in Arzneimittel Forschung, Vol. 9, page 765 (1959), is a criterion for establishing neuroleptic activity.

When the compounds were tested in comparative experiments with rats, the duration of the resulting blocking of apomorphine emesis and cataleptic activities were definitely prolonged.

The compounds of the present invention can be prepared by esterification of an alcohol consisting of an 8-substituted 10-[4-(hydroxyalkyl)piperazino]-10,11-dihydrodibenzo[b,f]thiepin or oxepin having the formula

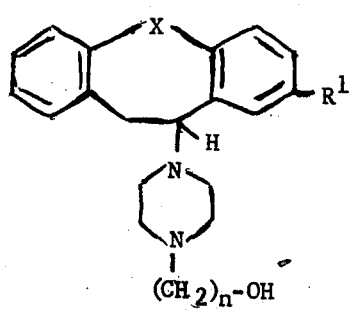

in which X, R¹ and n each have the same significance as defined hereinbefore by reaction with a fatty acid having the formula

R²—COOH in which R² has the same significance as defined hereinbefore, or a reactive derivative thereof, preferably a chloride, bromide, or anhydride of the fatty acid.

The 8-substituted 10-[4-(acyloxyalkyl)piperazino]-dibenzo[b,f]thiepins and oxepins and 4-[4-(acyloxyalkyl)piperazino]thieno[2,3-b]-1-benzothiepins and oxepins can be made in the same manner from the corresponding alcohols having the following formulae:

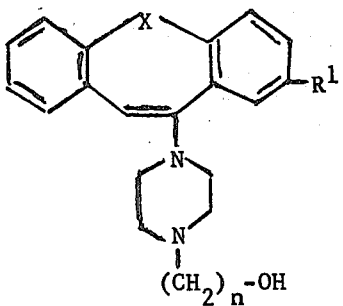

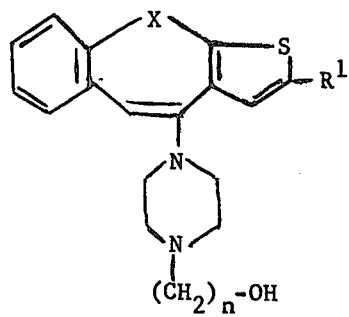

in which X, R¹ and n each have the same significance as defined hereinbefore.

The resulting esters can be converted into salts by reaction with an inorganic or organic acid.

When a fatty acid having the formula

R²—COOH is to be used for esterification, the reaction is preferably conducted in an inert solvent and in the presence of dicyclohexylcarbodiimide or N,N'-carbonyldiamidazole, preferably in a solvent consisting of a mixture of benzene and chloroform at a temperature between 20° and 120°C.

When a chloride of the fatty acid having the formula R²—COCl, or a bromide or an anhydride of the fatty acid, is to be used for the esterification, the reaction is preferably carried out in an inert solvent or mixture of inert solvents, such as a mixture of benzene and chloroform, or in a solvent such as a tertiary amine such as, for example, pyridine or triethylamine, which simultaneously acts as a condensing agent, and preferably at a temperature between 20° and 100°C.

8-Substituted 10-[4-(hydroxyalkyl)piperazino]-10,11-dihydrodibenzo[b,f]thiepins and oxepins which can be used as starting materials for the preparation of the compounds of the present invention and methods for their preparation are described in the article by J. O. Jilek, J. Pomykacek, J. Metysova and M. Protiva in Collection of Czechoslovak Chemical Communications, vol. 36, pages 2226–2247 (June 1971), and German Patent Application No. 2,014,199, published Oct. 1, 1970, and in U.S. Pat. No. 3,725,409, which issued on an application corresponding to German Patent Application No. 2,014,199. In accordance with the processes described therein 8-methylthio-10-[4-(3-hydroxypropyl)piperzino]-10,11-dihydrodibenzo[f,b]-thiepin, for example, was prepared by heating a mixture of 8-methyl-10-chloro-10,11-dihydrodibenzo[b,f]-thiepin and 1-(3-hydroxypropyl)piperazine at a temperature between 100° and 125°C for 3 hours.

In a similar manner can be prepared the following 8-substituted 10-[4-(hydroxyalkyl)piperazino]-10,11-dihydrodibenzo[b,f]thiepins and oxepins from which esters can be prepared which have also exhibited neuroleptic activity:

8-chloro-10-[4-(3-hydroxypropyl)piperazino]-10,11-dihydrodibenzo[b,f]thiepin,
8-chloro-10-[4-(4-hydroxybutyl)piperazino]-10,11-dihydrodibenzo [b,f]thiepin,
8-methoxy-10-[4-(3-hydroxypropyl)piperazino]-10,11-dihydrodibenzo[b,f]thiepin,
8methylthio-10-[4-(3-hydroxypropyl)piperazino]-10,11-dihydrodibenzo[b,f]oxepin,
8ethyl-10-[4-(3-hydroxypropyl)piperazino]-10,11-dihydrodibenzo[b,f]thiepin,
8-isopropyl-10-[4-(2-hydroxyethyl)piperazino]-10,11-dihydrodibenzo[b,f]thiepin,
8-isopropyl-10-[4-(4-hydroxybutyl)piperazino]-10,11-dihydrodibenzo[b,f]thiepin,
8-[n-butyl]-10-[4-(3-hydroxypropyl)piperazino]-10,11-dihydrodibenzo[b,f]thiepin,
8-cyclopropyl-10-[4-(3-hydroxypropyl)piperazino]-10,11-dihydrodibenzo[b,f]thiepin,
8cyclopentyl-10-[4-(3-hydroxypropyl)piperazino]-10,11-dihydrodibenzo[b,f]thiepin, and
8methyl-10-[4-(2-hydroxyethyl)piperazino]-10,11-dihydrodibenzo[b,f]oxepin.

Alcohols from which the related 8-substituted 10-[4-(acyloxyalkyl)piperazino]dibenzo[b,f]thiepins and oxepins and 4-[4-(acyloxyalkyl)piperazino]thieno[2,3-b]-1-benzothiepins and oxepins can be made are the following:

8-chloro-10-[4-(3-hydroxypropyl)piperazino]dibenzo[b,f]thiepin,
8-methoxy-10-[4-(3-hydroxypropyl)piperazino]dibenzo[b,f]thiepin,
8-methylthio-10-[4-(3-hydroxypropyl)piperazino]dibenzo[b,f]thiepin, and
4-[4-(3-hydroxypropyl)piperazino[thieno[2,3-b]-1-benzothiepin.

Acids which are suitable as such or in the form of chlorides, bromides, or anhydrides, for use in preparation of the compounds of the present invention in accordance with the processes hereinbefore described include, for example, caproic (hexanoic), enanthic (heptanoic), caprylic (octanoic), pelargonic (nonanoic), capric (decanoic), undecylic (hendecanoic), lauric (dodecanoic), myristic (tetradecanoic), palmitic (hexadecanoic) and stearic (octadecanoic) acids.

The compounds of the present invention is most instances are very viscous oils which, on standing and cooling, solidify into wax-like bodies. They can be converted into salts by reaction with inorganic and organic acids. These salts are generally crystalline and the compounds of the present invention can accordingly be obtained in highly purified form by recrystallization of such salts. The bases can then be recovered in pure form from such salts which have been purified by recrystallization and can then be used for the preparation of therapeutic compositions consisting essentially of solutions of the compounds in vegetable oils.

DETAILED DESCRIPTION AND PREFERRED EMBODIMENTS OF THE INVENTION

The invention is further described in the Examples which follow, which were selected solely for purposes of illustration. Consequently, it is to be understood that the invention is not restricted thereto and that alterations and modifications may be made therein in accordance with the teachings herein without departing from its scope.

EXAMPLE 1

8-Chloro-10-[4-(3-heptanoyloxypropyl)piperazino]-10,-11-dihydrodibenzo[b,f]thiepin A solution of 8 grams of enanthyl chloride (heptanoyl chloride), having a boiling point of 170–174°C at a pressure of 740 torr, in 20 milliliters of benzene was introduced into a solution of 7.8 grams of 8-chloro-10-[4-(3-hydroxypropyl)piperazino]-10,11-dihydrodibenzo[b,f]thiepin in a mixture of 10 milliliters of chloroform and 30 milliliters of benzene. The mixture warmed up spontaneously and a gel-like mass separated therein. This mixture was allowed to stand without stirring for 4 days at room temperature. Thereafter the mixture was diluted with 100 milliliters of benzene and 100 milliliters of water. To this mixture was then added 8 milliliters of concentrated aqueous ammonium hydroxide solution and the resultant mixture was shaken thoroughly. The benzene phase, which contained the desired product, was separated from the aqueous phase, washed with water, dried over anhydrous potassium carbonate, and the solvent was then evaporated therefrom. The residue, which amounted to 12.0 grams, was a semisolid mass which, after thin-layer chromatography on alumina, contained none of the starting compound. The entire reaction product thus obtained was then dissolved in 50 milliliters of acetone and added to a solution of 5.6 grams of maleic acid in 25 milliliters of acetone, whereupon 13.2 grams of crude salt separated. This salt was recrystallized twice from an aqueous solution of acetone containing 90% by volume of acetone. The recrystallized compound had a melting point of 149–150°C and its elemental analysis corresponded to the empirical formula $C_{36}H_{45}ClN_2O_{10}S$ (molecular weight 733.3). This compound was 8-chloro-10-[4-(3-heptanoyloxypropyl)-piperazino]-10,11-dihydrodibenzo[b,f]thiepin di(hydrogen maleate).

To a suspension in water of 9.2 grams of the thus recrystallized pure di(hydrogen maleate) was added 8 milliliters of concentrated aqueous ammonium hydroxide solution and the reaction mixture was then shaken and extracted with benzene. The benzene extract was dried over anhydrous potassium carbonate, filtered, and the benzene was then evaporated therefrom. The solvent that still remained in the residue was expelled by heating the residue at a temperature of 70°C for a long period in a high vacuum. About 6.5 grams of a very viscous oil consisting of pure 8-chloro-10-[4-(3-heptanoyloxypropyl)piperazino]-10,11-dihydrodibenzo[b,f]thiepin was thus recovered. A solution in sunflower oil which could be directly used as a medicament was prepared from this compound.

EXAMPLE 2

8-Methoxy-10-[4-(3-octanoyloxypropyl)piperazino]-10,11-dihydrodibenzo[b,f]thiepin To a solution of 14.82 grams of 8-methoxy-10-[4-(3-hydroxypropyl)piperazino]-10,11-dihydrodibenzo[b,f]thiepin in 50 milliliters of benzene was added 12.55 grams of caprylic acid (octanoic acid). The resulting reaction mixture was allowed to stand overnight and was then heated for 3 hours at a temperature of 60°C. After cooling, the mixture was shaken with 100 milliliters of water, 20 milliliters of concentrated aqueous ammonium hydroxide solution was then added thereto, and the mixture was extracted with a mixture of benzene and ethyl ether. The resulting extract was washed with water, dried over anhydrous potassium carbonate, and the solvent was evaporated therefrom. The residue was dissolved in 40 milliliters of acetone and added to a solution of 9.5 grams of maleic acid in 30 milliliters of acetone. On standing, 15.5 grams of crude 8-methoxy-10-]4-(3-octanoyloxypropyl)-piperazino]-10,11-dihydrobenzo[b,f]thiepin di(hydrogen maleate) crystals separated therefrom. On purification by recrystallization from acetone, the di(hydrogen maleate) salt had a melting point of 130°C. The free base was recovered in the form of a viscous oil by adding the di(hydrogen maleate) to a dilute aqueous ammonium hydroxide solution and extracting the solution with benzene as described in Example 1 hereinbefore.

EXAMPLE 3

8-Methoxy-10-[4-(3-dodecanoyloxypropyl)-piperazino]-10,11-dihydrodibenzo[b,f]thiepin In accordance with the procedure described in the foregoing Examples, 12.96 grams of 8-methoxy-10-[4-(3-hydroxypropyl)piperazino]-10,11-dihydrodibenzo[b,f]thiepin was reacted with 13.1 grams of lauroyl chloride (dodecanoyl chloride) in 50 milliliters of benzene and the resulting crude 8-methoxy-10-[4-(3-dodecanoyloxypropyl)piperazino]-10,11-dihydrodibenzo[b,f]thiepin was purified by recrystallization of the maleate from acetone and recovered in the form of its di(hydrogen maleate). The salt was recovered in a yield of 14.9 grams and had a melting point of 126–129°C. The pure ester was recovered in the form of a viscous oil by adding the salt to a dilute aqueous ammonium hydroxide solution and extracting the resulting solution with benzene.

EXAMPLE 4

8-Methylthio-10-[4-(3-heptanoyloxypropyl)-piperazino]-10-11-dihydrodibenzo[b,f]thiepin To a solution of 14.0 grams of 8-methylthio-10-[4-(3-hydroxypropyl)piperazino]-10,11-dihydrodibenzo[b,f]thiepin in a mixture of 20 milliliters of choroform and 60 milliliters of benzene was added 10.8 grams of enanthyl chloride (heptanoyl chloride) and the resulting mixture was allowed to stand for 4 days at room temperature. The mixture was then added to 100 milliliters of water, to which 8 milliliters of concentrated aqueous ammonium hydroxide solution was then added and the resulting solution was extracted with benzene. After washing the extract with water, drying it over anhydrous potassium carbonate, and evaporating the solvent, a residue consisting of crude 8-methylthio-10-[4-(3-heptanoyloxypropyl)piperazino]-10,11-dihydrodibenzo[b,f]thiepin was obtained. To this residue was added a solution of 8.65 grams of maleic acid in 100 milliliters of acetone, and 18.0 grams of the crystalline di(hydrogen maleate) salt was separated therefrom. This salt, when recrystallized from acetone, had a melting point of 126–128°C. By adding 20 milliliters of concentrated aqueous ammonium hydroxide solution to a solution of 16.1 grams of this purified salt in 200 milliliters of water, followed by extraction of the solution with benzene, and evaporation of the benzene from the extract, 9.6 grams of an oily base was obtained. This base was chromatographically homogeneous but could not be crystallized even after standing for a long period at room temperature.

EXAMPLE 5

8-Methylthio-10-[4-(3-octanoyloxypropyl)-piperazino]-10,11-dihydrodibenzo[b,f]thiepin In accordance with the general procedure described in the foregoing Examples, 14.0 grams of 8-methylthio-10-[4-(3-hydroxypropyl)piperazino]-10,11-dihydrodibenzo[b,f]thiepin was reacted with 12.2 grams of caprylyl chloride (octanoyl chloride) in a mixture of 20 milliliters of chloroform and 60 milliliters of benzene. After the reaction mixture had been allowed to stand for 4 days at room temperature, the reaction mixture was heated to a temperature of 60°C and further treated as described in the preceding Example. The recovered crude 8-methylthio-10-[4-(3-octanoyloxypropyl)piperazino]-10,11-dihydrodibenzo[b,f]thiepin was thereafter converted into the crystalline di(hydrogen maleate) as described in the foregoing Example. The salt was recovered in a yield of 13.7 grams and, after recrystallization from acetone, had a melting point of 122°–123°C. The pure base was recovered in the form of a viscous oil by treatment of the pure salt with a dilute aqueous solution of ammonium hydroxide as described in the foregoing Example.

EXAMPLE 6

8-Methylthio-10-[4-(3-dodecanoyloxypropyl)-piperazino]-10,11-dihydrodibenzo[b,f]thiepin In accordance with the general procedure described in the foregoing Examples, 14.0 grams of 8-methylthio-10-[4-(3-hydroxypropyl)piperazino]-10,11-dihydrodibenzo[b,f]thiepin was reacted with 15.3 grams of lauroyl chloride (dodecanoyl chloride) in a mixture of benzene and chloroform. In this manner, 8-methylthio-10-[4-(3-dodecanoyloxypropyl)piperazino]-10,11-dihydrodibenzo[b,f]thiepin was obtained. The pure base was a viscous oil which formed a crystalline di(hydrogen maleate) that had a melting point of 121°–122°C, after recrystallization from acetone.

EXAMPLE 7

8-Methylthio-10-[4-(3-hexadecanoyloxypropyl)-piperazino]-10,11-dihydrodibenzo[b,f]thiepin To a solution of 14.0 grams of 8-methylthio-10-[4-(3-hydroxypropyl)piperazino]-10,11-dihydrodibenzo[b,f]thiepin in a mixture of 20 milliliters of chloroform and 60 milliliters of benzene was added 19.2 grams of palmitoyl chloride (hexadecanoyl chloride) and the mixture was allowed to stand at room temperature overnight. Thereafter the mixture was heated at a temperature of 60°C for a period of 2 hours. After cooling, the mixture was added to 100 milliliters of water containing 10 milliliters of concentrated aqueous ammonium hydroxide solution, and the mixture was extracted with benzene. The extract was then washed with water, dried over anhydrous potassium carbonate, and the solvent was evaporated therefrom. The residue which included the desired ester was dissolved as completely as possible in benzene and the solution was subjected to chromatographic separation in an alumina column which was then eluted with benzene. From the benzene extract, 14.4 grams of pure 8-methylthio-10-[4-(3-hexadecanoyloxypropyl)piperazino]-10,11-dihydrodibenzo[b,f]thiepin was recovered. The palmitic acid with which the product was contaminated was substantially completely adsorbed on the alumina column. The crude base was converted into the crystalline di(hydrogen maleate) in accordance with the general procedure described in the foregoing Examples. The yield of the salt which, after recrystallization from acetone, had a melting point of 126°–127°C, was 14.4 grams. The pure base was recovered in the form of a colorless viscous liquid by subsequent treatment of the salt with a dilute aqueous ammonium hydroxide solution and extraction with benzene.

EXAMPLE 8

8-Ethyl-10-[4-(3-octanoyloxypropyl)piperazino]-10,11-dihydrodibenzo[b,f]thiepin

To a solution of 11.4 grams of 8-ethyl-10-[4-(3-hydroxypropyl)piperazino]-10,11-dihydrodibenzo[b,f]thiepin in a mixture of 60 milliliters of benzene and 20 milliliters of chloroform was added 10.5 grams of caprylyl chloride (octanoyl choride) and the resultant mixture was allowed to stand for 4 days at room temperature. Thereafter the mixture was heated for 1 hour at a temperature of 60°C. After cooling, 100 milliliters of water and 20 milliliters of concentrated aqueous ammonium hydroxide solution was added thereto and the resulting mixture was extracted with benzene. The extract was washed with water, dried with anhydrous potassium carbonate, and the solvent was evaporated therefrom. The residue which was thus recovered was dissolved in 50 milliliters of acetone and a solution of 9.2 grams of maleic acid in 30 milliliters of acetone was added thereto. From this solution the di(hydrogen maleate) of 8-ethyl-10-[4-(3-octanoyloxypropyl)-piperazino]-10,11-dihydrodibenzo[b,f]thiepin separated and was recovered by suction filtration, washed with ethyl ether, and recrystallized from acetone.

In this manner 13.0 grams of the salt, which had a melting point of 144°–146°C, and whose elemental analysis corresponded to the empirical formula $C_{39}H_{52}N_2O_{10}S$, was obtained. By adding the salt to a dilute aqueous solution of ammonium hydroxide and extracting the resulting solution with benzene, the free base was formed and recovered from the benzene extract as a colorless viscous oil which was very soluble in vegetable oils.

EXAMPLE 9

8-Ethyl-10-[4-(3-dodecanoyloxypropyl)piperazino]-10,11-dihydrodibenzo[b,f]thiepin In accordance with the general method described in the foregoing Examples, 10.15 grams of 8-ethyl-10-[4-(3-hydroxypropyl)piperazino]-10,11-dihydrodibenzo[b,f]thiepin was reacted with a solution of 12.5 grams of lauroyl chloride (dodecanoyl chloride) in a mixture of 60 milliliters of benzene and 20 milliliters of chloroform. By adding a solution of 6.15 grams of maleic acid in 60 milliliters of acetone to the crude product, 14.0 grams of 8-ethyl-10-[4-(3-dodecanoyloxypropyl)piperazino]-10,11-dihydrodibenzo[b,f]thiepin di(hydrogen maleate) was recovered. The salt, after recrystallization from acetone, had a melting point of 126°–128°C. Its elemental analysis corresponded to the empirical formula $C_{43}H_{60}N_2O_{10}S$. The free base was obtained in the form of a colorless very viscous oil which was very soluble in vegetable oils by dissolving the salt in a dilute aqueous ammonium hydroxide solution and extracting the resulting solution with benzene.

This base, as well as most of the other bases which are described herein, can also be recovered by extracting the solution with chloroform instead of benzene.

EXAMPLE 10

8-(n-Butyl)-10-[4-(3-octanoyloxypropyl)piperazino]-10,11-dihydrodibenzo[b,f]thiepin In accordance with the general procedure described in the foregoing Examples, 4.1 grams of 8-(n-butyl)-10-[4-(3-hydroxypropyl)piperazino]-10,11-dihydrodibenzo[b,f]thiepin was reacted with 3.2 grams of caprylyl chloride (octanoyl chloride) in a mixture of 18 milliliters of benzene and 7 milliliters of chloroform. A solution of 2.3 grams of maleic acid in 25 milliliters of acetone was then added to the mixture and the resulting 8-(n-butyl)-10-[4-(3-oxtanoyloxypropyl)piperazino]-10,11-dihydrodibenzo[b,f]thiepin di(hydrogen maleate) which had a melting point of 113°–115°C, after recrystallization from acetone, was recovered. Its elemental analysis corresponded to the empirical formula $C_{41}H_{56}N_2O_{10}S$. The free base was obtained in the form of a colorless very viscous oil which was very soluble in vegetable oils by dissolving the salt in a dilute aqueous ammonium hydroxide solution and extracting the solution with benzene.

EXAMPLE 11

8-Methyl-10-[4-(2-decanoyloxyethyl)piperazino]-10,11-dihydrodibenzo[b,f]oxepin

In accordance with the general procedure described in the foregoing Examples, 3.4 grams of 8-methyl-10-[4-(2-hydroxyethyl)piperazino]-10,11-dihydrodibenzo[b,f]oxepin was reacted with 4.0 grams of capric acid chloride (decanoyl chloride) in 40 milliliters of benzene. The reaction mixture was treated as described in Example 8 to recover the base as crude 8-methyl-10-[4-(2-decanoyloxyethyl)piperazino]-10,11-dihydrodibenzo[b,f]oxepin therefrom. This crude base was then added to a solution of maleic acid in acetone and the corresponding di(hydrogen maleate) that was thus formed was recovered and purified by recrystallization from acetone. It has a melting point of 135°–137°C and its elemental analysis corresponded to the empirical formula $C_{39}H_{52}N_2O_{11}$. By treating this salt as described in the preceding Examples, the free base was recovered as a colorless, very viscous oil, which was very soluble in vegetable oils.

EXAMPLE 12

8-Methyl-10-[4-(2-tetradecanoyloxyethyl)piperazino]-10,11-dihydrodibenzo[b,f]oxepin In accordance with the general procedure described in the foregoing Examples, 2.06 grams of 8-methyl-10-[4-(2-hydroxyethyl)piperazino]-10,11-dihydrodibenzo[b,f]oxepin was reacted with a solution of 3.0 grams of myristoyl chloride (tetradecanoyl chloride) in 25 milliliters of benzene. The reaction mixture was treated as described in Example 8 to recover the base as crude 8-methyl-10-[4-(2-tetradecanoyloxyethyl)piperazino]-10,11-dihydrodibenzo[b,f]oxepin therefrom. The crude base was then added to a solution of maleic acid in acetone and the di(hydrogen maleate) salt that was thus formed was recovered and purified by recrystallization from acetone. It had a melting point of 139°–141°C and its elemental analysis corresponded to the empirical formula $C_{43}H_{60}N_2O_{11}$. By treating this salt as described in the foregoing Examples, the free base was recovered as a substantially colorless oil which was very viscous and which was very soluble in vegetable oils.

EXAMPLE 13

8-Methylthio-10-[4-(3-decanoyloxypropyl)piperazino]-10,11-dihydrodibenzo[b,f]thiepin In accordance with the general procedure described in the foregoing Examples, 14.0 grams of 8-methylthio-10-[4-(3-hydroxypropyl)piperazino]-10,11-dihydrodibenzo[b,f]thiepin was reacted with 14.3 grams of capric acid chloride (decanoyl chloride) in a mixture of 20 milliliters of chloroform and 60 milliliters of benzene. The mixture was left for 4 days at room temperature and was then heated for 1 hour at a temperature of 60°C. After cooling, the reaction mixture was added to 100 milliliters of water, 20 milliliters of concentrated aqueous ammonium hydroxide solution was then added thereto, and the solution was then extracted with 100 milliliters of benzene. The benzene extract was then washed with water, dried over anhydrous potassium carbonate, and the benzene evaporated therefrom, leaving a residue consisting of crude 8-methylthio-10-[4-(3-decanoyloxypropyl)piperazino]-10,11-dihydrodibenzo[b,f]thiepin. To this residue was then added a solution of 8.65 grams of maleic acid in 100 milliliters of acetone, from which solution the di(hydrogen maleate) salt crystallized. After recrystallization from acetone, this salt had a melting point of 120°–121°C and its elemental analysis conformed to the empirical formula $C_{40}H_{54}N_2O_{10}S_2$ (molecular weight 787.0). By adding 20 milliliters of concentrated aqueous ammonium hydroxide solution to a solution of this pure salt in 200 milliliters of water, followed by extraction with benzene, and evaporation of the benzene from the extract, the oily base was obtained.

EXAMPLE 14

8-Chloro-10-[4-(3-heptanoyloxypropyl)piperazino]-dibenzo[b,f]thiepin

To a solution of 4.6 grams of 8-chloro-10-[4-(3-hydroxypropyl)piperazino]dibenzo[b,f]thiepin in 7 milliliters of chloroform and 20 milliliters of benzene was added 3.5 grams of enanthyl chloride (heptanoyl chloride) and the resulting mixture was allowed to stand for 4 days at room temperature. Thereafter 50 milliliters of water and 5 milliliters of concentrated aqueous ammonium hydroxide solution was added thereto. The resulting mixture was extracted by shaking with benzene. The benzene extract was separated from the aqueous phase, washed with water, dried over anhydrous potassium carbonate, and the benzene was evaporated therefrom. The oily residue was dissolved in 12 milliliters of acetone and to the solution was added a solution of 3.0 grams of maleic acid in 8 milliliters of acetone. After concentration of the resulting reaction mixture by evaporation, the residue was diluted with ethyl ether. The 8-chloro-10-[4-(3-heptanoyloxypropyl)piperazino]dibenzo[b,f]thiepin di(-hydrogen maleate) salt that was thus formed, precipitated from the solution and was then separated therefrom. This crude product, weighing 6.9 grams, was purified by recrystallization from dioxane to produce a product having a melting point of 141°–142°C, which by elemental analysis was established to be a hemihydrate having the empirical formula $C_{36}H_{43}ClN_2O_{10}S.½\lambda H_2O$. The base that was obtained by adding a dilute aqueous ammonium hydroxide solution to this salt and extracting the solution with chloroform was a very viscous colorless oil which was very soluble in vegetable oils.

EXAMPLE 15

8-Methoxy-10-[4-(3-octanoyloxypropyl)piperazino]-dibenzo[b,f]thiepin

To a solution of 10.0 grams of 8-methoxy-10-[4-(3-hydroxypropyl)piperazino]dibenzo[b,f]thiepin in 50 milliliters of benzene was added 9.1 grams of caprylyl chloride (octanoyl chloride) and the mixture was allowed to stand for 48 hours. Thereafter 150 milliliters of water and 20 milliliters of concentrated aqueous ammonium hydroxide solution was added thereto and the resulting mixture was shaken with benzene. The benzene extract was separated form the aqueous solution, filtered, and the filtrate was washed with water, dried over anhydrous potassium carbonate, and the benzene was evaporated therefrom. The residue was dissolved in 30 milliliters of acetone and to this solution was added a solution of 2.9 grams of maleic acid in 10 milliliters of acetone.

The resulting clear solution was concentrated by evaporation and to the resulting concentrated solution ethyl ether was added, producing a precipitation of 14.4 grams of crude 8-methoxy-10-[4-(3-octanoyloxypropyl)piperazino]dibenzo[b,f]thiepin maleate which was sepaprated by suction filtration. After recrystallization of the crude precipitate from a mixture of ethyl acetate and ethyl ether a purified product having a melting point of 125°–126°C, whose elemental analysis conformed to the empirical formula $C_{34}H_{44}N_2O_7S$, was obtained. The free base was recovered as a very viscous colorless oil that was very soluble in vegetable oils by adding a dilute aqueous ammonium hydroxide solution to the salt and extracting the solution with chloroform.

EXAMPLE 16

4-[4-(3-Octanoyloxypropyl)piperazino]thieno[2,3-b]-1-benzothiepin

In accordance with the general prodecure described in the preceding Examples, 7.6 grams of 4-[4-(3-hydroxypropyl)piperazino]thieno[2,3-b]-1-benzothiepin was reacted with 8.6 grams of caprylyl chloride (octanoyl chloride) in 100 milliliters of benzene. After treatment with water and concentrated ammonium hydroxide solution, the solution was extracted with benzene and the benzene was evaporated therefrom. The residue was dissolved in acetone and a solution of 2.4 grams of maleic acid in 30 milliliters of acetone was added thereto. The crude 4-[4-(3-octanoyloxypropyl)-piperazino]thieno[2,3-b]-1-benzothiepin maleate that was thus produced, weighing 7.6 grams, was separated by suction filtration and recrystallized from a mixture of acetone and ethyl ether. The purified product had a melting point of 146.5°–148.5°C and its elemental analysis corresponded to the empirical formula $C_{31}H_{40}N_2O_6S_2$. The free base was recovered as a very viscous colorless oil which was very soluble in vegetable oils by adding a dilute aqueous ammonium hydroxide solution to the salt, extracting the solution with chloroform, and evaporating the chloroform from the extract.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:
1. 8-methylthio-10-[4-(3-decanoyloxypropyl)-piperazino]-10,11-dihydrodibenzo[b,f]thiepin.
2. A maleic acid salt of the compound defined in claim 1.

* * * * *